United States Patent [19]

Castagna

[11] Patent Number: 5,195,975
[45] Date of Patent: Mar. 23, 1993

[54] SINGLE USE HYPODERMIC SYRINGE
[76] Inventor: John F. Castagna, 200 W. Sarah St., Milford, Pa. 18337
[21] Appl. No.: 820,917
[22] Filed: Jan. 15, 1992
[51] Int. Cl.$^5$ .............................................. A61M 5/00
[52] U.S. Cl. ..................... 604/110; 604/218; 604/228
[58] Field of Search ................ 604/110, 187, 218, 228

[56] References Cited
U.S. PATENT DOCUMENTS

| | | | |
|---|---|---|---|
| 4,775,363 | 10/1988 | Sandsdalen | 604/110 |
| 4,883,466 | 11/1989 | Glazier | 604/228 X |
| 4,915,692 | 4/1990 | Verlier | 604/218 X |
| 4,923,443 | 5/1990 | Greenwood et al. | 604/110 |
| 4,950,243 | 8/1990 | Estruch | 604/218 X |
| 5,066,280 | 11/1991 | Braithwaite | 604/110 |

*Primary Examiner*—John D. Yasko

[57] ABSTRACT

A hypodermic syringe comprises a barrel, a plunger slidably received in the barrel, a drive shaft slidable in the barrel, and a connector for drivably connecting the drive shaft to the plunger. The connector has a plunger end including a first pair of resilient fingers insertable into the plunger, a drive shaft end having second pair of fingers insertable into the drive shaft, and an intermediate portion intermediate the plunger and drive shaft ends. The first pair of fingers has projections which engage apertures in the plunger. The second pair of fingers engages an annular rib in the drive shaft. When the drive shaft is fully inserted into the barrel to bottom the plunger, the drive shaft slides over the first pair of fingers, causing the fingers to retract and the projections to disengage from the apertures in the plunger. The connector remains engaged with the drive shaft, and separates from the plunger the drive shaft is withdrawn from the barrel, thereby preventing further use of the syringe.

19 Claims, 2 Drawing Sheets

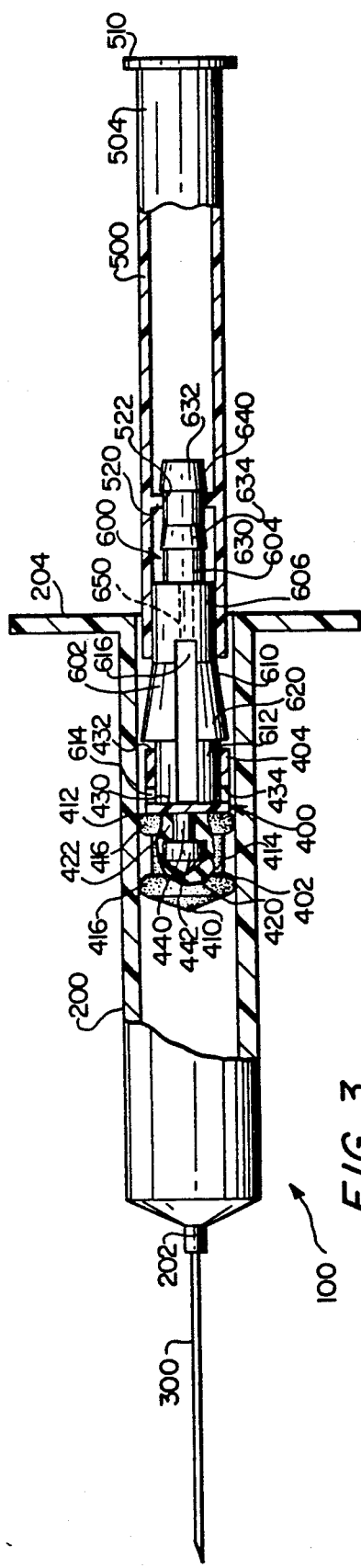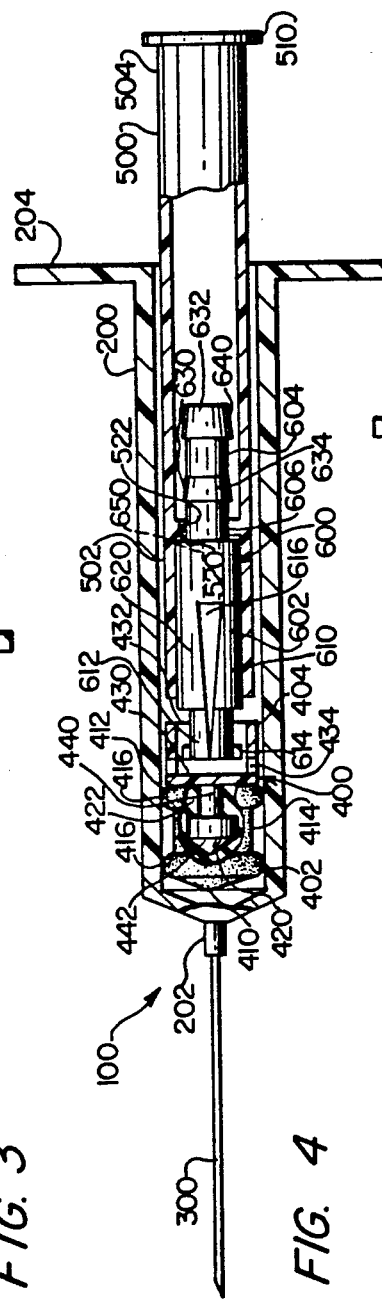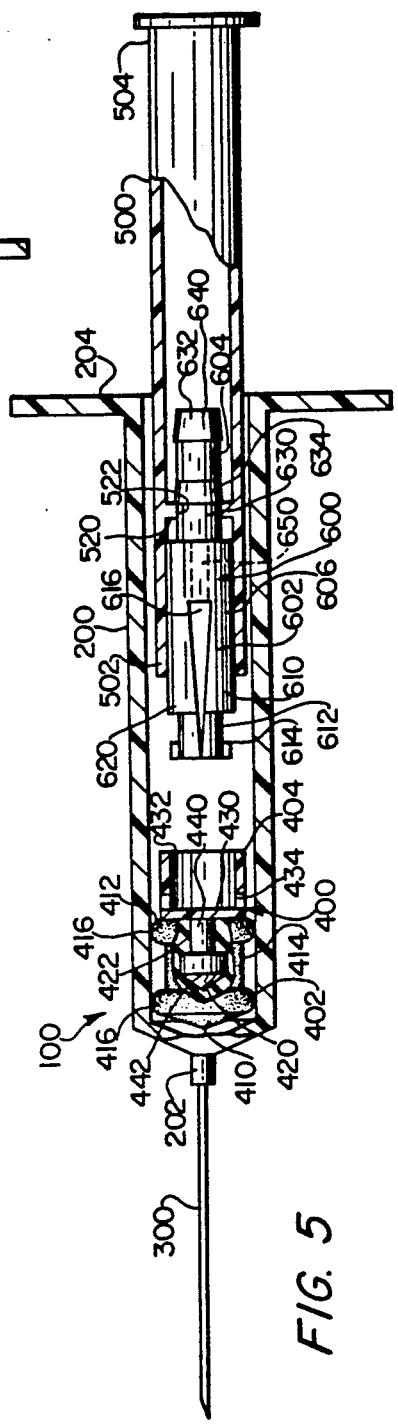

SINGLE USE HYPODERMIC SYRINGE

BACKGROUND OF THE INVENTION

1. Field of the Invention

The present invention relates to hypodermic syringes. More specifically, the invention relates to hypodermic syringes which are usable only a single time.

2. Related Art

Syringes which are commonly in use do not have any mechanism for preventing their re-use. Because many serious diseases, most notably Acquired Immune Deficiency Syndrome and hepatitis, can be spread by re-use of syringes, it is desirable that syringes be incapable of more than a single use. It is to the solution of this and other problems to which the present invention is directed.

SUMMARY OF THE INVENTION

It is therefore a primary object of the present invention to provide a hypodermic syringe which is capable of only a single use.

This and other objects of the invention are achieved by the provision of a hypodermic syringe which comprises a barrel, a plunger slidably received in the barrel, a drive shaft slidable in the barrel, and a connector for drivably connecting the drive shaft to the plunger. The connector includes disengaging means for disengaging the connector from the plunger when the drive shaft is moved from a retracted position to an inserted position.

In particular, the connector has a plunger end including a first pair of resilient fingers insertable into the plunger, a drive shaft end having second pair of fingers insertable into the drive shaft, and an intermediate portion intermediate the plunger and drive shaft ends. The first pair of fingers has projections which engage apertures in the plunger. The second pair of fingers engages an annular rib in the drive shaft. When the drive shaft is fully inserted into the barrel to bottom the plunger, the drive shaft slides over the first pair of fingers, causing the fingers to retract and the projections to disengage from the apertures in the plunger. The connector remains engaged with the drive shaft, and separates from the plunger when the drive shaft is withdrawn from the barrel, thereby preventing further use of the syringe.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIG. 3 is a cross-sectional view of the syringe of FIG. 1, assembled and in position for the administration of an injection.

FIG. 4 is a cross-sectional view of the syringe of FIG. 1, assembled and in position following the administration of an injection.

FIG. 5 is a cross-sectional view of the syringe of FIG. 1, disassembled following the administration of an injection.

DETAILED DESCRIPTION OF THE PREFERRED EMBODIMENTS

Figure 1:
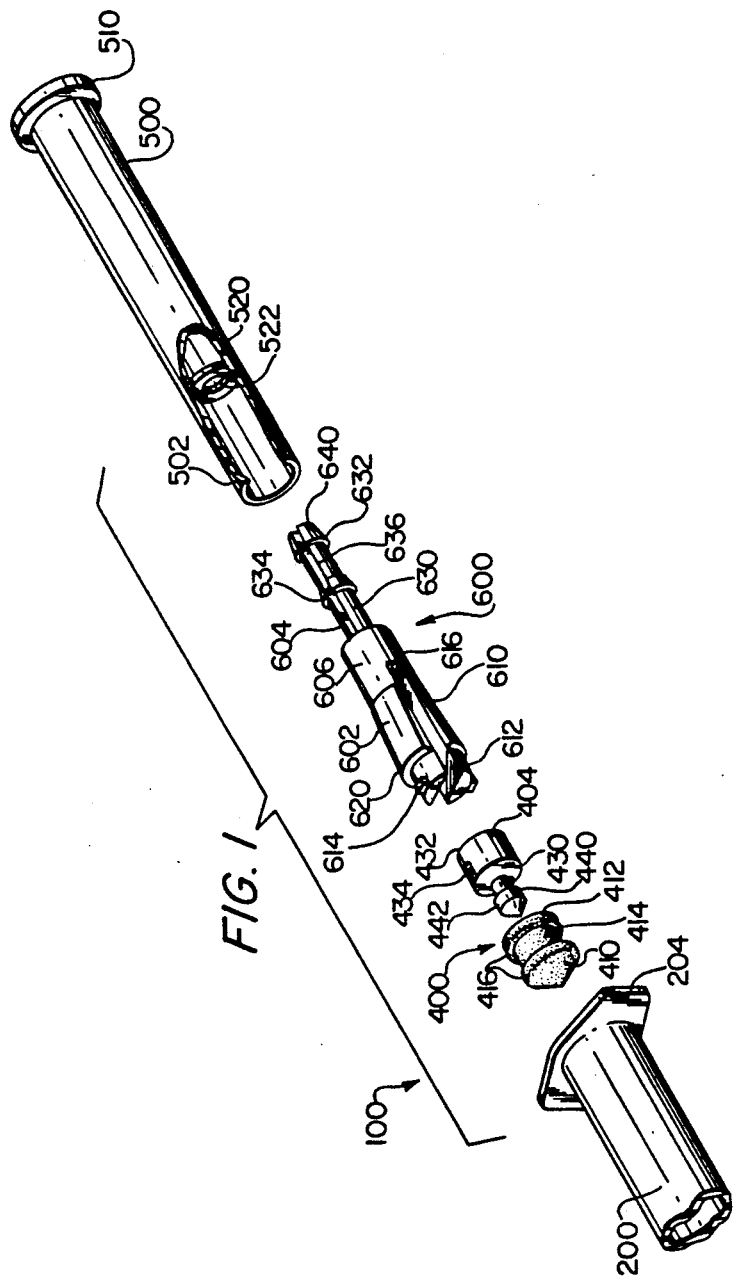
FIG. 1 is an exploded perspective view of a single-use hypodermic syringe according to the invention.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

Figure 2:
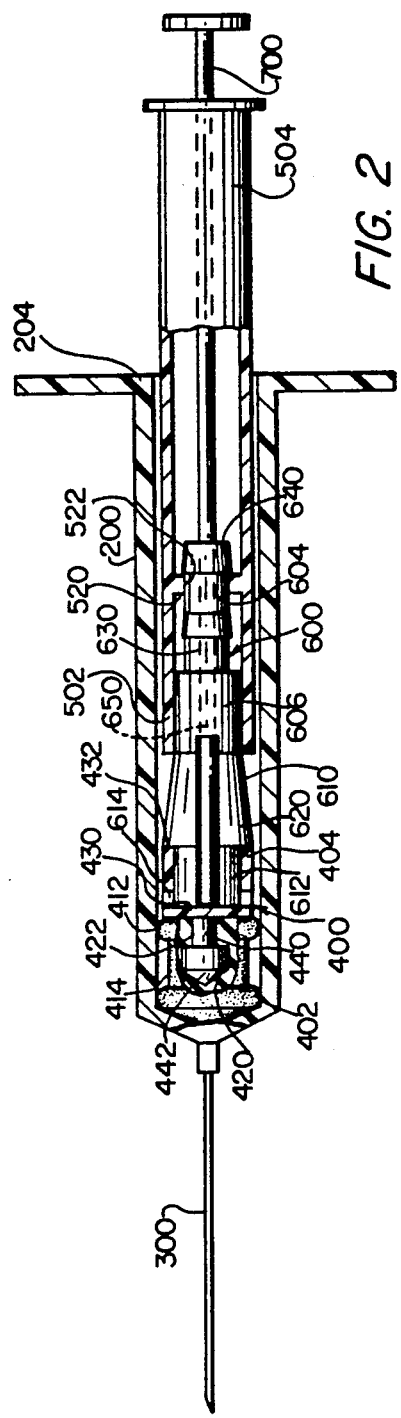
FIG. 2 is a cross-sectional view of the syringe of FIG. 1, shown in the process of being assembled.

Referring now to FIGS. 1-5, there is shown a single-use hypodermic syringe 100 comprising a conventional barrel 200, a conventional needle 300, a plunger 400 slidable within barrel 200, a drive shaft 500, and a connector 600 drivably connecting drive shaft 500 to plunger 400.

Barrel 200 has a needle end 202 for receiving needle 300 and a drive shaft and 204 for receiving drive shaft 500.

Plunger 400 has a two-piece construction comprising a bottom sealing section 402 inserted into barrel 200 facing needle end 202 and a top connecting section 404 inserted into barrel 200 facing drive shaft end 204. Sealing section 402 I5 preferably is made from rubber or another material having similar properties of flexibility, resilience, and impermeability to liquids, and has a conical end 410 for engagement with needle end 202, a flattened end 412 opposite conical end 410, and a reduced-diameter portion 414 intermediate conical end 410 and flattened end 412. The difference in diameter between reduced-diameter portion 414 and conical and flattened ends 410 and 412 defines a pair of spaced-apart annular lips 416 which flex as they sealingly engage the inner surface of barrel 200. Sealing section 402 must be lubricated in order to operate properly.

Reduced-diameter portion 414 is formed with a hollow interior 420 and flattened end 412 is formed with an aperture 422 therethrough in communication with and having a smaller diameter than interior 420, for a purpose to be described hereinafter.

Connecting section 404 preferably is made from a hard plastic material and comprises a hollow cylindrical body having a closed end 430 and an open end 432. A pair of opposed apertures 434 are formed through the side wall of connecting section 404 in communication with the interior of connecting section 404. A shaft 440 terminating in an enlarged head 442 extends perpendicularly from closed end 430 for engagement with hollow interior 420 and aperture 422 of sealing section 402.

Hollow interior 420 and aperture 422 and the one hand, and shaft 440 and head 442 on the other hand define female and male parts of a snap-fit connecting means between sealing section 402 and connecting section 404. The resilience of sealing section 402 in combination with the tapering of the distal end of head 442 permits the insertion of head 442 through aperture 442 with relative ease, while the flattening of the proximal end of head 442 in combination with the small diameter of aperture 442 prevents withdrawal of head 442 from interior 420 without the exertion of considerable effort.

Drive shaft 500 has an inner end 502 inserted into barrel 200 facing needle end 202 and an outer end 504 which extends out of drive shaft end 204 of barrel 200 when drive shaft 500 is inserted into barrel 200. A lip 510 is formed at outer end 504 to act as a stop when drive shaft 500 is inserted into barrel 200. An annular rib 520 is formed in the inner wall of drive shaft 500 inwardly of inner end 504. Annular rib 520 defines a circular aperture 522, for a purpose to be described hereinafter.

Connector 600 has a plunger end 602 insertable into the interior of connecting section 404 through open end 432, a drive shaft end 604 insertable into inner end 502 of drive shaft 500, and an intermediate portion 606 intermediate plunger and drive shaft ends 602 and 604.

Plunger end 602 includes an inner portion 610 and an outer portion 612. Inner portion 610 has a generally frustoconical shape tapering inwardly towards central portion 606 and has a maximum diameter smaller than the inner diameter of barrel 200, larger than the inner diameter of drive shaft 500, and at least as large as the outer diameter of connecting section 404 of plunger 400. Outer portion 612 has a generally cylindrical shape of circular cross-section, and has a diameter approximately equal to the inner diameter of connecting section 404. Thus, outer portion 612 can be inserted into the interior of connecting section 404 through open end 432.

A pair of opposed projections 614 extend radially from outer portion 612 for engagement with axial recesses 422. A slot 616 of substantially rectangular prismatic shape is formed along a diameter of plunger end 602 perpendicular to a line defined by projections 614, to define a first pair of resilient fingers 620, for a purpose to be described hereinafter.

Drive shaft end 604 includes an inner portion 630 having a generally cylindrical shape of circular cross-section and having a diameter smaller than the inner diameter of drive shaft 500, to permit inner portion 630 to slide freely within circular aperture 522 formed in drive shaft 500. Drive shaft end 604 also includes an outer portion 632 and retaining ring 634 formed centrally on inner portion 630. Both outer portio 632 and retaining ring 634 have a generally frustoconical shape tapering outwardly towards central portion 606 and have a maximum diameter greater than the diameter of aperture 522. A slot 636 of substantially rectangular prismatic shape is formed along a diameter of drive shaft end 604 perpendicular to slot 616 to define a second a pair resilient fingers 640, also for a purpose to be described hereinafter.

Intermediate portion 606 has a generally cylindrical shape and has a diameter substantially equal to or less than the inner diameter of drive shaft 500 to permit central portion 606 to slide within drive shaft 500. An axial cylindrical bore 650 is formed through intermediate portion 606 of connector 600, for a purpose to be described hereinafter. Bore 650 communicates with both of slots 616 and 636.

All components of syringe 100 are made using materials conventionally used for syringe components and are easily moldable by ordinary techniques. It is contemplated that barrel 200, connecting section 404 of plunger 400, drive shaft 500, and connector 600 can, for example, be made using polystyrene, acrylic, nylon, or any other plastic material which will not interact with the fluid to be drawn into barrel 200, and which will meet the strength, temperature, humidity and other requirements for syringe components.

Syringe 100 is assembled in the following manner. First, sealing section 402 is connected to connecting section 404 by inserting head 442 into interior 420. Connector 600 is assembled to plunger 400 by urging fingers 620 together, enabling them to be inserted into open end 432 of connection section 404. When fingers 620 are released, projections 614 engage radial recesses 422, securing connector 600 to plunger 400.

Connector 600 is assembled to drive shaft 500 by inserting drive shaft end 604 of connector 600 into inner end 502 of drive shaft 500. Outer portion 632 of drive shaft end 604 engages aperture 522 of drive shaft 500, the taper of outer portion 632 functioning as a wedge to cause fingers 640 to be urged towards each other. The diameter of outer portion 632 is thus decreased, allowing it to pass through aperture 522. At this time, connector 600 is not inserted far enough into drive shaft 500 to permit locking ring 634 to engage aperture 522.

As soon as outer portion 632 has completely passed through aperture 522, fingers 640 return to their original position. As a result, outer portion 632 positively engages annular rib 520, providing a locking engagement between connector 600 and drive shaft 500 which prevents connector 60 from becoming disengaged from drive shaft 500.

Once connector 600 is assembled to plunger 400 and drive shaft 500, a thin rod 700 is inserted into slot 636, through axial bore 650, and into slot 616. Plunger 400 can then be bottomed in barrel 200 by pushing on drive shaft 500, and rod 700 will prevent fingers 620 from collapsing inwardly. After plunger 400 has been bottomed in barrel 200, rod 700 is removed and syringe 100 is ready for use.

In use, fluid is drawn into barrel 200 in the conventional manner by retracting drive shaft 500. Because plunger 400 is linked to drive shaft 500 by connector 600, retraction of drive shaft 500 results in retraction of plunger 400. When plunger 400 is again bottomed in barrel 200 in the course of injecting the fluid, the conical configuration of inner portion 610 of plunger end 602 of connector 600 permits inner end 502 of drive shaft 500 to slide over inner portion 610, causing fingers 620 to be urged towards each other. Simultaneously, inner portion 630 of drive shaft end 602 of connector 600 slides in aperture 522 towards outer end of 504 of drive shaft 500, causing locking ring 634 to pass through aperture 522.

When plunger 400 is fully bottomed, inner end 502 of drive shaft 500 bears against open end 432 of connecting section 404, and fully encloses frustoconical inner portion 602 of connector 602. As a result, fingers 620 are fully compressed, causing projections 614 to be withdrawn from radial recesses 422, and plunger 400 to be released from engagement with connector 600. Thus, when drive shaft 500 is retracted, connector 600 separates from plunger 400. Further, the flattened face of locking ring 634 locks connector 60 into its retracted position within drive shaft 500, and thus prevents fingers 620 from returning to their original, uncompressed state. Thus, when drive shaft 500 is withdrawn from barrel 600, fingers 620 remain enclosed within inner end 502 of drive shaft 500, and cannot re-engage with plunger 400, thereby preventing reuse of syringe 100.

It is noted that rod 700 is inserted only for manufacturing purposes, to prevent fingers 620 from collapsing when plunger 400 is initially bottomed, and that rod 700 is intended to be removed immediately following the initial bottoming of plunger 400. Syringe 100 is sold with plunger 400 fully bottomed, and plunger 400 can be withdrawn once without disengagement from connector 600. Disengagement occurs when plunger 400 is bottomed a second time.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

What is claimed is:

1. A single-use hypodermic syringe comprising:
a barrel having a needle end and a drive shaft end;
a plunger slidably received in said barrel and having a bottom and a top, said bottom facing said needle end of said barrel and said top facing said drive shaft end of said plunger;
a drive shaft received in said barrel through said drive shaft end and slidable in said barrel between an inserted position and a withdrawn position; and
connecting means for drivably connecting said drive shaft to said plunger, said connecting means including disengaging means for disengaging said connecting means from said plunger when said drive shaft is moved from said retracted position to said inserted position to bottom said plunger in said barrel, wherein said disengagine means comprising a pair of resilient fingers movable between a spaced-apart position and a collapsed position, said fingers in the extended position engaging said plunger, and wherein at least a portion of said fingers is received within said drive shaft when said drive shaft is in said inserted position, to move said fingers into said collapsed position, whereby said fingers are disengaged from said plunger.

2. The syringe of claim 1, wherein said plunger includes a radial recess in said top for receiving said fingers.

3. The syringe of claim 1, wherein said connecting means includes retaining means for retaining said fingers within said drive shaft when said drive shaft is moved from said inserted position back to said retracted position.

4. The syringe of claim 1, wherein said top and bottom of said plunger are formed as separated pieces, and wherein said top and bottom include male and female connecting means for connecting them together.

5. A single-use hypodermic syringe comprising:
a barrel having a needle end and a drive shaft end;
a plunger slidably received in said barrel and having a bottom and a top, said bottom facing said needle end of said barrel and said top facing said drive shaft end of said plunger;
a drive shaft received in said barrel through said drive shaft end and slidable in said barrel between an inserted position and a withdrawn position; and
connecting means for drivably connecting said drive shaft to said plunger, said connecting means including disengaging means for disengaging said connecting means from said plunger when said drive shaft is moved from said retracted position to said inserted position to bottom said plunger in said barrel, wherein said disengagine means comprises first and second pairs of spaced-apart fingers at opposite ends of said connecting means, and wherein the inner wall of said drive shaft and said second pair of fingers include interengagement means for retaining said second pair of finges in said drive shaft, and wherein said top of said plunger and said first pair of fingers include interengagement means for releasably retaining said first pair of fingers in said top of said plunger, at least a portion of said first pair of fingers being slidable in said inner end of said drive shaft.

6. A single-use hypodermic syringe comprising:
a barrel having a needle end and a drive shaft end;
a plunger slidably received in said barrel and having a bottom and a top, said bottom facing said needle end of said barrel and said top facing said drive shaft end of said plunger, and said top having an axial recess therein and at least two radial apertures therein in communication with said axial recess;
a drive shaft received in said barrel through said drive shaft end and slidable in said barrel between an inserted position and a withdrawn position, said drive shaft having an inner end facing said needle end of said barrel and an outer end extending out of said drive shaft end of said barrel; and
a connector slidable within said inner end of said drive shaft and having a first end releasably engageable with said axial recess of said plunger and a second end retained in said outer end of said drive shaft, said first end including disengaging means for disengaging said first end of said connector from said plunger when said drive shaft is moved from said retracted position to said inserted position to bottom said plunger in said barrel and said connector slides within said drive shaft.

7. The syringe of claim 6, wherein said disengaging means comprises a pair of resilient fingers movable between a spaced-apart position and a collapsed position, said fingers in the extended position engaging said axial recess of said plunger, and wherein said fingers move into said collapsed position when said connector slides within said drive shaft, whereby said fingers are disengaged from said plunger.

8. The syringe of claim 7, wherein said second end of said connector includes retaining means for retaining said fingers within said drive shaft when said drive shaft is moved from said inserted position back to said retracted position.

9. The syringe of claim 6, wherein said second end of said connector includes a pair of spaced-apart fingers and wherein the inner wall of said drive shaft and said fingers include interengagement means for retaining said fingers in said drive shaft.

10. The syringe of claim 6, wherein said first end of said connector includes a pair of spaced-apart fingers and wherein said top of said plunger and said fingers include interengagement means for releasably retaining said fingers in said top of said plunger, at least a portion of said fingers being slidable in said inner end of said drive shaft.

11. A single-use hypodermic syringe, comprising:
a barrel having a needle end and a drive shaft end;
a plunger having a bottom sealing section inserted into said barrel facing said needle end and a top connecting section inserted into said barrel facing said drive shaft end, said top connecting section having an axial recess formed therein;
a drive shaft having an inner end inserted into said barrel facing said needle end and an outer end extending out of said drive shaft end of said barrel when said drive shaft is inserted into said barrel, wherein said drive shaft has an annular rib formed in the inner wall thereof inwardly of said inner end, said annular rib defining a circular aperture; and
a connector having a plunger end releasably engageable with said axial recess of said top connecting section of said plunger and a drive shaft end engageable with said inner end of said drive shaft, wherein said drive shaft end of said connector includes a pair of spaced apart-fingers having an inner portion and an outer portion, said outer portion having a generally frustoconical shape for engaging said circular aperture.

12. The syringe of claim 11, wherein said top connecting section and said bottom sealing section of said plunger are formed as separated pieces, and wherein said top connecting section and said bottom sealing section include male and female connecting means for connecting them together.

13. The syringe of claim 11, wherein said top connecting section is formed of a relatively hard plastic material and said bottom sealing section is formed of a rubber material.

14. The syringe of claim 13, wherein said inner portion has a generally frustoconcial ring formed centrally thereon for engaging said circular aperture.

15. A single-use hypodermic syringe, comprising:
a barrel having a needle end and a drive shaft end;
a plunger having a bottom sealing section inserted into said barrel facing said needle end and a top connecting section inserted into said barrel facing said drive shaft end, said top connecting section having an axial recess formed therein;
a drive shaft having an inner end inserted into said barrel facing said needle end and an outer end extending out of said drive shaft end of said barrel when said drive shaft is inserted into said barrel, and
a connector having a plunger end releasably engageable with said axial recess of said top connecting section of said plunger and a drive shaft end engageable with said inner end of said drive shaft, wherein said plunger end of said connector includes a pair of spaced apart-fingers having an inner portion and an outer portion, and wherein said outer portion has a generally cylindrical shape for insertion into said axial recess of said plunger and said inner portion has a generally frustoconical shape, the maximum diameter of said inner portion being greater than the inner diameter of said axial recess and larger than the inner diameter of said drive shaft.

16. The syringe of claim 15, wherein said top connecting section has radial apertures formed in the side wall thereof in communication with said axial recess, and wherein said fingers have projections extending radially therefrom for engagement with said axial recesses.

17. A single-use hypodermic syringe, comprising:
a barrel having a needle end and a drive shaft end;
a plunger having a bottom sealing section inserted into said barrel facing said needle end and a top connecting section inserted into said barrel facing said drive shaft end, said top connecting section having an axial recess formed therein;
a drive shaft having an inner end inserted into said barrel facing said needle end and an outer end extending out of said drive shaft end of said barrel when said drive shaft is inserted into said barrel, and
a connector having a plunger end releasably engageable with said axial recess of said top connecting section of said plunger and a drive shaft end engageable with said inner end of said drive shaft, wherein said drive shaft end of said connector includes a pair of spaced apart-fingers having an inner wall of said drive shaft and said finges include interengagement means for retaining said fingers in said drive shaft.

18. A single-use hypodermic syringe, comprising:
a barrel having a needle end and a drive shaft end;
a plunger having a bottom sealing section inserted into said barrel facing said needle end and a top connecting section inserted into said barrel facing said drive shaft end, said top connecting section having an axial recess formed therein;
a drive shaft having an inner end inserted into said barrel facing said needle end and an outer end extending out of said drive shaft end of said barrel when said drive shaft is inserted into said barrel, and
a connector having a plunger end releasably engageable with said axial recess of said top connecting section of said plunger and a drive shaft end engageable with said inner end of said drive shaft, wherein said plunger end of said connector includes a pair of spaced-apart fingers and wherein said top connecting section of said plunger and said fingers include interengagement means for releasably retaining said fingers in said top connecting section, at least a portion of said fingers being slidable in said inner end of said drive shaft.

19. A method of assembling a single-use hypodermic syringe, comprising the steps of:
(a) providing a barrel having a needle end and a drive shaft end;
(b) providing a plunger having a bottom sealing section and a top connecting section, the top connecting section having an axial recess formed therein;
(c) providing a drive shaft having an inner end and an outer end;
(d) providing a connector having a plunger end including a first pair of longitudinally-extending spaced-apart fingers, a drive shaft end including a second pair of longitudinally-extending spaced-apart fingers, and an intermediate portion intermediate the plunger end and the drive shaft end, the intermediate portion having an axial bore extending therethrough in communication with the spaces between the first fingers and the second fingers;
(e) inserting the first and second pairs of fingers of the connector into the radial aperture of the plunger and the inner end of the drive shaft, respectively, to drivingly connect the plunger to the drive shaft;
(f) inserting the thin rod into the space between the second pair of fingers of the connector, through the axial bore in the intermediate portion of the connector, and into the space between the first pair of fingers of the connector;
(g) inserting the assembled plunger, connector, and drive shaft into the barrel with the bottom sealing section of the plunger facing the needle end of the barrel and the oute end of the drive shaft extending out of the drive shaft end of the barrel while the thin rod is in place in the spaces between the first and second pairs of fingers and the axial bore of the connector;
(h) bottoming the plunger in the barrel by pushing down on the outer end of the drive shaft while the thin rod is in place in the spaces between the first and second pairs of fingers and the axial bore of the connector; and
(i) removing the thin rod.

* * * * *